US008491660B2

(12) United States Patent
Kaiser et al.

(10) Patent No.: US 8,491,660 B2
(45) Date of Patent: Jul. 23, 2013

(54) HYBRID ELECTROMAGNETIC-ACOUSTIC DISTAL TARGETING SYSTEM (75) Inventors: Edgar J. Kaiser, Probsteierhagen (DE); Andreas Werner Speitling, Kiel (DE)

(73) Assignee: Stryker Trauma GmbH (DE)

( * ) Notice: Subject to any disclaimer, the term of this patent is extended or adjusted under 35 U.S.C. 154(b) by 1217 days.

(21) Appl. No.: 11/883,475

(22) PCT Filed: Mar. 30, 2006

(86) PCT No.: PCT/EP2006/002904
§ 371 (c)(1),
(2), (4) Date: Jul. 24, 2007

(87) PCT Pub. No.: WO2006/103071
PCT Pub. Date: Oct. 5, 2006

(65) Prior Publication Data
US 2008/0170473 A1    Jul. 17, 2008

(30) Foreign Application Priority Data

Mar. 31, 2005  (DE) .................. 10 2005 014 573
Mar. 31, 2005  (DE) .................. 20 2005 009 809 U (51) Int. Cl.
*A61F 2/30*  (2006.01)
*A61B 5/05*  (2006.01)
*A61B 19/00* (2006.01)

(52) U.S. Cl.
USPC ........ 623/18.11; 600/407; 600/427; 128/899; 128/903

(58) Field of Classification Search
USPC .................... 623/13.16; 128/903; 600/300
See application file for complete search history.

(56) References Cited

U.S. PATENT DOCUMENTS

| 11,365 A | 7/1859 | Fishwick et al. |
| 34,355 A | 2/1862 | Fairbanks |
| 4,304,077 A | 12/1981 | Muller |
| 4,494,950 A | 1/1985 | Fischell |

(Continued)

FOREIGN PATENT DOCUMENTS

| AU | 2003213476 A1 | 2/2004 |
| AU | 2003264218 A1 | 4/2005 |

(Continued)

OTHER PUBLICATIONS

"Loads Acting in an Intramedullary Nail During Fracture Healing in the Human Femur", E. Schneider et al., Journal of Biomechanics 34, 2001, pp. 849-857.

(Continued)

*Primary Examiner* — Thomas J Sweet
*Assistant Examiner* — Joshua Levine
(74) *Attorney, Agent, or Firm* — Lerner, David, Littenberg, Krumholz & Mentlik, LLP (57) ABSTRACT A data transmission system connected to a bone implant has an extra-corporeally arranged external transmitting unit an implantable internal first receiving unit adapted to be actuated by the external transmitting unit. An internal transmitting unit is adapted to be coupled and implanted to the implant. A second transmission section is located between the external transmitting unit and the internal first receiving unit, via which the internal transmitting unit is actuated. A second receiving unit and a first transmission section is located between the internal transmitting unit and the second receiving unit. The first transmission section operates with acoustic vibrations or waves.

27 Claims, 3 Drawing Sheets

U.S. PATENT DOCUMENTS

| | | | |
|---|---|---|---|
| 4,622,644 A | 11/1986 | Hansen | |
| 4,849,692 A | 7/1989 | Blood | |
| 4,945,305 A | 7/1990 | Blood | |
| 5,049,151 A | 9/1991 | Durham et al. | |
| 5,113,859 A | 5/1992 | Funke | |
| 5,127,913 A | 7/1992 | Thomas, Jr. | |
| 5,411,503 A | 5/1995 | Hollstien et al. | |
| 5,453,686 A | 9/1995 | Anderson | |
| 5,514,145 A | 5/1996 | Durham et al. | |
| 5,584,838 A | 12/1996 | Rona et al. | |
| 5,707,375 A | 1/1998 | Durham et al. | |
| 5,904,708 A | 5/1999 | Goedeke | |
| 6,039,742 A | 3/2000 | Krettek et al. | |
| 6,074,394 A | 6/2000 | Krause | |
| 6,162,228 A | 12/2000 | Durham | |
| 6,185,452 B1 | 2/2001 | Schulman et al. | |
| 6,447,448 B1* | 9/2002 | Ishikawa et al. | 600/300 |
| 6,579,244 B2 | 6/2003 | Goodwin | |
| 6,616,670 B2 | 9/2003 | Simon et al. | |
| 6,620,101 B2 | 9/2003 | Azzam et al. | |
| 6,628,989 B1 | 9/2003 | Penner et al. | |
| 6,849,047 B2 | 2/2005 | Goodwin | |
| 7,015,859 B2 | 3/2006 | Anderson | |
| 7,060,075 B2 | 6/2006 | Govari et al. | |
| 7,190,273 B2 | 3/2007 | Liao et al. | |
| 7,397,364 B2 | 7/2008 | Govari | |
| 2003/0040806 A1* | 2/2003 | MacDonald | 623/23.49 |
| 2003/0078495 A1 | 4/2003 | Goodwin | |
| 2003/0112598 A1 | 6/2003 | Yokosawa | |
| 2003/0139690 A1 | 7/2003 | Aebli et al. | |
| 2004/0011365 A1 | 1/2004 | Govari et al. | |
| 2004/0034355 A1 | 2/2004 | Govari et al. | |
| 2004/0062258 A1 | 4/2004 | Grow et al. | |
| 2004/0158299 A1 | 8/2004 | Patrias | |
| 2004/0186396 A1* | 9/2004 | Roy et al. | 600/594 |
| 2004/0204744 A1* | 10/2004 | Penner et al. | 607/23 |
| 2004/0245821 A1 | 12/2004 | Chen | |
| 2005/0010300 A1 | 1/2005 | Disilvestro et al. | |
| 2005/0012610 A1 | 1/2005 | Liao et al. | |
| 2005/0026113 A1 | 2/2005 | Chen et al. | |
| 2005/0080427 A1 | 4/2005 | Govari et al. | |
| 2005/0099290 A1 | 5/2005 | Govari | |
| 2005/0101866 A1 | 5/2005 | Goodwin | |
| 2005/0104776 A1 | 5/2005 | Anderson | |

FOREIGN PATENT DOCUMENTS

| | | |
|---|---|---|
| CA | 2464433 | 5/2003 |
| CA | 2435464 | 1/2004 |
| DE | 2715106 | 10/1978 |
| DE | 3332642 | 4/1985 |
| DE | 102004054914 A1 | 6/2005 |
| DE | 202005009809 | 9/2005 |
| DE | 102005014573 A1 | 10/2006 |
| EA | 0408805 | 1/1991 |
| EP | 0362611 A1 | 4/1990 |
| EP | 1195143 | 4/2002 |
| EP | 1382308 A2 | 1/2004 |
| EP | 1508302 | 2/2005 |
| GB | 2408805 A | 6/2005 |
| JP | 2000-183828 A | 6/2000 |
| JP | 2002-506700 T | 3/2002 |
| JP | 2003-070752 A | 3/2003 |
| JP | 2004-130094 | 4/2004 |
| JP | 2004-511313 T | 4/2004 |
| JP | 2005-506867 | 3/2005 |
| KR | 20040010240 | 1/2004 |
| WO | WO-93/02626 | 2/1993 |
| WO | WO-97/13467 | 4/1997 |
| WO | WO-01/05314 A1 | 1/2001 |
| WO | 02/09113 | 1/2002 |
| WO | WO-03/009772 | 2/2003 |
| WO | WO-03/034922 A1 | 5/2003 |
| WO | WO-03/043688 | 5/2003 |
| WO | WO-2005/027745 | 3/2005 |
| WO | WO-2006/103071 A1 | 10/2006 |

OTHER PUBLICATIONS

"e-Knee: Evolution of the Electronic Knee Prosthesis: Telemetry Technology Development", B. Morris et al., The Journal of Bone and Joint Surgery, 2001, 83, pp. 62-66.

"Concept, Design and Fabrication of Smart Orthopedic Implants", F. Burny et al., Medical Engineering & Physics, 22, 2000, pp. 469-479.

"Monitoring In Vivo Implant Loads With a Telemeterized Internal Spinal Fixation Device", A. Rohlmann et al., Spine, vol. 25, No. 23, pp. 2981-2986, Nov. 23 , 2000.

"A Low Power Miniaturized Autonomous Data Logger for Dental Implants", W. Claes et al., Sensors and Actuators, A 97-98, 2002, pp. 548-556.

* cited by examiner

HYBRID ELECTROMAGNETIC-ACOUSTIC DISTAL TARGETING SYSTEM

TECHNICAL FIELD

The invention relates to a data transmission system connected to an implant measuring system connected to an implant.

BACKGROUND OF THE INVENTION

A wide variety of intramedullary and extramedullary bone implants, such as plates, nails or the like are used mainly to treat fractures. A distinction is generally made between implants with a transcutaneous transit and those which are implanted without a transcutaneous transit. The former include, for example, external fixators and the latter nails or plates.

A method is known for determining physical and/or chemical values in connection with an implant. For example, it is desirable to determine the static and dynamic load of implants. A method is known from the "Journal of Biomechanics 34" (2001) pp. 849-857 for arranging a receiver coil for receiving external energy, a measuring circuit, a wire resistance strain gauge, a data converter circuit and a transmitting circuit and coil in a so-called interlocking bone nail. These elements are designed to record the forces acting on the bone. A method is known from "The Journal of Bone and Joint Surgery", Volume 83-A Supplement 2, Part 1 (2001), pp. 62-65, for installing the wire resistance strain gauge in a knee prosthesis and connecting it by cable to an extracorporeal measuring instrument. A method is known from "Medical Engineering & Physics 22" (2000), pp. 469-479, for installing wire resistance strain gauges, e.g. in the case of a femur strap, and to connect them by cable to an extracorporeal measuring instrument. A method for measuring the force acting on vertebral column implants was published in "SPINE", Volume 25, no. 23, pp. 2981-2986, and load measurements were also made known in connection with dental prosthesis in "Sensors and Actuators" A 97-98 (2002), pp. 548-556.

In all data recording systems connected to implants the transmission of the measured values externally is required. For this purpose use is made, for example, of wires which connect the measuring unit to a measuring instrument or measured value processing unit. Although such a system is not too restrictive to the wearer of the implant, under certain circumstances, provided that the measuring instrument is fixed comfortably on the outside, the feeding of lines through bones and soft tissues may cause constant irritations and even inflammations. If possible and justifiable in terms of cost, wireless telemetry, i.e. the wireless transmission of measured data extracorporeally, is preferable as the method of choice. Such a wireless transmission is described, for example, in the article in "Medical Engineering & Physics" 22 already referred to.

Inductive or capacitive couplings to suitable magnetic and electrical antennae are used at low frequencies for the transmission path in the near field. If electromagnetic far field antennae are used, this involves high frequencies. The transmission path may either lead from the data recording system in the direction of the implant ("uplink") or from the implant in the direction of the data recording system ("downlink"). The uplink section is often used to supply energy to the implanted system by inductive coupling.

One disadvantage of telemetry systems of prior art is the considerable attenuation of the electromagnetic waves generated during transit through a metal screen. Additionally the attenuation of electromagnetic waves as they are propagating through free space or tissue or materials of any kind is significant.

A further disadvantage consists in the difficulty in realising the transmitting unit (miniaturisation). The screening has a particularly detrimental effect when high frequencies of over 1 MHz are used for transmitting high data rates. Since implantable telemetry systems are preferably integrated in metal capsules of titanium or implant steel, for reasons of tissue compatibility and economy, telemetry is regarded as problematic.

SUMMARY OF THE INVENTION

An object of the invention is to provide a measuring system connected to an implant, which enables the transfer of data.

The object may be solved by a data transmission system connected to an implant according to the independent claim.

In a first exemplary embodiment a data transmission system is provided. The data transmission system comprises an extracorporeally arranged external transmitting unit, an implantable internal first receiving unit adapted to be actuated by the external transmitting unit, an internal transmitting unit adapted to be coupled and implanted to the implant, a second transmission section between the external transmitting unit and the internal first receiving unit, via which the internal transmitting unit is actuated, a second receiving unit, and a first transmission section between the internal transmitting unit and the second receiving unit. Thereby, the first transmission section operates with acoustic vibrations or waves.

The advantage of the measuring system according to the invention lies in the fact that acoustic vibrations may also penetrate metal screens with low damping. Acoustic waves are also able to propagate with low damping in metal implants and bone and/or soft tissue. Therefore not only the implant, but also the bone and soft part tissues of the implant wearer, may be used as a transmission medium for acoustic telemetry. According to one design of the invention it is therefore advantageous for the internal transmitting unit to be coupled acoustically to the implant. If the implant is arranged intracorporeally, the external transmitting unit and/or the acoustic second receiving unit receiving unit can be designed for application to the skin. For example, a housing receiving these parts may be suitably fastened to the body part concerned. An acoustic transmitting unit may also be easily miniaturised in a non-metallic enclosure.

In a further exemplary embodiment, the second transmission section operates with electromagnetic waves.

Thus, in a further exemplary embodiment, the second transmission section is adapted for transmitting both data and energy for operating the internal receiving unit and/or the internal transmitting unit. Energy or data information may be sent from the external transmitting unit to the implant respectively the internal first receiving unit. A method of also implanting the energy source to an implant for telemetry connected to an implant, and dispensing with an external energy supply and external control, is indeed conceivable. This would normally be regarded as only one exception. The use of an uplink and a downlink is typical. The uplink to an external transmitting unit and an internal intracorporeal receiving unit normally serves to transmit control signals to the measuring unit and also to the transmitter for the downlink. Furthermore, this guarantees the energy supply, particularly through inductive coupling. The intracorporeal transmitting unit for the downlink is encapsulated completely in metal, for example, and communicates with an extracorporeal external receiving unit. Encapsulation into non-metallic materials, such as, but not limited to polymers, glasses, ceramics is also considered. There are therefore two wireless transmission sections. According to the invention at least the transmission section between the internal transmitting unit and external receiving unit is designed for acoustic data transmission. The data determined by the measuring unit are converted in the downlink receiver to acoustic data or used for actuating an acoustic converter for transmission to the extracorporeal receiving unit. It is indeed also conceivable to utilise acoustic transmission for the other transmission section (uplink), which could be useful for the control data, whilst the electromagnetic coupling is preferable for the external electrical energy supply.

In a further exemplary embodiment, the transmitting unit comprises at least one transmitting coil for transmitting data and energy via the second transmission section. For transmitting electromagnetic energy, the transmitting device may be equipped with transmitting coils that are adapted to send electromagnetic energy to the implant or the first internal receiving unit. The transmitting coils send electromagnetic energy with predetermined frequencies and signal strength. By using different frequencies several kind of information may be sent to the implant and an improved spatial information of the transmitting coil with respect to the first internal receiving unit may be determined.

In a further exemplary embodiment, the first receiving unit comprises a receiving coil.

The receiving coils are adapted to transform the electromagnetic energy in electric current or voltage respectively to the signal strength or frequencies. Thus, several kind of information may be transmitted.

In a further exemplary embodiment, the internal transmitting unit consists of a first acoustic transducer element. The first acoustic transducer element may transform the signals received from the first internal receiving unit in acoustic waves or ultra sound waves according to the signal strength and frequencies. Thus, several kind of information may be transmitted. The acoustic waves may transmitted along the implant, wherein for example comparing to electromagnetic waves, the interference and the absorbability of these acoustic waves by the implant is reduced.

In a further exemplary embodiment, the second receiving unit comprises an acoustic transducer element and a transmitting element. Thereby, the acoustic transducer element is adapted for transforming acoustic waves into electrical signals, wherein the transmitting element is adapted for transmitting the electric signal to the external transmitting unit via a third transmitting section. The second receiving unit, respectively the acoustic transducer, may receive the acoustic waves sent along the implant by the internal transmitting unit, and transforms the acoustic energy into electric signals according to the frequencies and signal strength of the acoustic waves. The second receiving unit may be adapted to be connected to one end of the implant or to the skin. In the major of cases, the second receiving unit is adapted to extracorporeal appliance.

In a further exemplary embodiment, the third transmission section is adapted for transmitting data by acoustic vibrations or waves, electric signals or electromagnetic waves, wherein the third transmitting section consists of a cable connection or a wireless connection. Therefore the second receiving unit may be connected to the external transmitting unit by cable or wireless. The second receiving unit may also be designed for integrally connection to the external receiving unit.

In a further exemplary embodiment, the data transmission system further comprises a processor unit. The processor unit is adapted for being fixed to the second receiving unit and/or to the external transmitting unit. Further on, the processor unit is adapted for evaluating the data received by the second receiving unit. The processor may evaluate the received data in order to process the data for example into data used for visualising.

In a further exemplary embodiment, the internal transmitting unit is acoustically coupled to the implant. By coupling the internal transmitting unit acoustically, the implant becomes conductor of the acoustic waves, so that a better data transfer may be possible.

In a further exemplary embodiment, the external transmitting unit and/or the second receiving unit are designed to be coupled acoustically to the skin and/or an external part of a transcutaneous implant. Thus the units may be aligned to the skin, without evoke negative effects of the skin or of the tissue. By coupling the units to the skin it may also possible, to receive or transmit the acoustic waves through the skin respectively the tissue to the implant. Thus, a direct contact of the implant with the transmitting unit or the second receiving unit is nor necessary.

In a further exemplary embodiment, the implant is an internal implant with transcutaneous transit, wherein the first transmission section is formed by means of a metal pin or the like. In the case of an implant with transcutaneous transit, e.g. an external fixator, the metal pins of the fixator may form the transmission section and the acoustic receiver may be installed in the distal region of the pins or at the points of application.

In a further exemplary embodiment, the internal transmitting unit and the first receiving unit are installed on an intramedullar, and the second receiving unit can be detachably installed on the associated end of the implant, the nail or on a driving-in instrument connected to the nail.

In a further exemplary embodiment, the data transmission system further comprises a measuring unit adapted to be implanted with the implant for measuring at least one physical or chemical value on the implant or in the region thereof. By implanting a measuring unit, several data may be measured, such as temperature, blood quality or healing status of the fracture. The measured data may be send to the second receiving unit and to the external transmitting unit by the internal transmitting unit for further processing.

In a further exemplary embodiment, the internal transmitting unit and/or the first internal receiving unit are integrated with the measuring unit or a transponder. The transponder is implanted and may be acoustically connected to the implant and energy is supplied by means of inductive and/or capacitive coupling along the uplink. The downlink, i.e. the first transmission section from the transponder to an second receiving unit, may take place acoustically.

In a further exemplary embodiment, data transmission system further comprises a transponder unit. The transponder unit comprises the first internal receiving unit and the internal transmitting unit and wherein the transponder unit is encapsulated in a body-compatible material.

In a further exemplary embodiment, the implantable transponder unit forms an independent unit or is integrated in the implant.

In a further exemplary embodiment, the implantable transponder unit is integrated in an implantable telemetry unit or is coupled to such a unit.

In a further exemplary embodiment, a data transmission takes place from the external transmitting unit to the implantable first transponder unit by means of electromagnetic vibrations and/or waves.

In a further exemplary embodiment, the internal transmitting unit is coupled acoustically to the bone, implant or soft part tissue.

In a further exemplary embodiment, one of the measuring unit and the implanted transponder contains a memory with permanently stored data. The memory may be a read-only memory unit or a modifiable writable memory.

In a further exemplary embodiment, the data transmission system comprising a further transponder unit. The transponder unit and the further transponder unit are located on the implant. The further transponder unit comprises an further internal receiving unit and a further internal transmitting unit. The external transmitting unit comprises a further transmitting coil for transmitting data and energy via the second transmission section to the further internal receiving unit of the further transponder unit. The receiving coils of the transponder unit respectively the further transponder unit are adapted for activating the internal transmitting units according to the transmitted data originating from the external transmitting unit. The internal transmitting units of the transponder unit and the further transponder unit transmit the data to the second receiving unit via the first transmission section. The second receiving unit or the transmitting unit are adapted for analysing the position of the transmitting unit relative to the transponder unit and the further transponder unit.

It is also possible, to install the measuring unit, the internal transmitting and receiving unit to an intramedullar nail, and to install the external acoustic receiving unit detachably at the turned end of the nail or on a driving-in and/or target instrument that can be connected to the nail. By installing at least two transponder units to the nail, the external transmitting unit is adapted to be used as targeting device for bores of the implant. Therefore, adjacent to each bore, two transponders are installed having the same distance to the bore axis. The external transmitting device, which may also be called as distal targeting device, comprises a plurality of transmitting coils. Each transmitting coils sends electromagnetic waves with a certain frequency and signal strength. The electromagnetic waves are received by receiving coils of the transponders and transformed the electromagnetic waves in acoustic waves. The acoustic waves have a frequency assigned to the frequency of the electromagnetic waves. The signal strength of the acoustic waves is assigned to the transmitted electro magnetic signal strength respectively the distance between the transmitting coils and the receiving coils. The acoustic waves are sent to the second receiving unit and further to for example a processor unit for processing the data. Based on the received frequencies, it can be determined from which transponder the data were sent and based on the signal strength, the distance of the distal targeting unit to the transponder can be measured. Thus, the distance of each transmitting coil to each receiving coil may be measured, so that the position of the distal targeting device relative to the bores may be determined precisely. The frequencies may be for example in the interval of 40 kHz to 70 kHz.

For determining the position of each bore in one dimension, two transmitting coils are necessary. By using six transmitting coils e.g. arranged in two triples of coils in two different planes, all parameters that are required to find the axis of the boreholes can be obtained. Other spatial arrangements of the transmitter coil array are possible. By using four pairs of transmitting coils or more, the quality of the targeting result may be further improved. For each degree of freedom, one pair of transmitting coils is necessary.

Instead of using different frequencies, the transmitting coils may send one frequency. Thereby, the transmitting coils are activated successively. This so called time multiplex measuring system may reduce the system complexity.

Further on, the distal targeting device may provide a digital coding system, wherein the signals transmitted by the different coils of the transmission coil array are digitally coded using different coding schemes. By using the digital coding, the received signals may be easily separated according to their origin from the different coils in the transmission coil array due to their digital coding. This so-called code multiplex or code-diversity signal approach can be advantageous in certain circumstances.

A method is known for transmitting data to a transponder (uplink) and in the other direction (downlink) using so-called RFID technology. However, the disadvantage of this is that it is easily susceptible to interference may in turn cause interferences, e.g. in safety systems. For example, false alarms may be triggered. The reliability of the data read-out is also improved by an acoustic downlink because an electromagnetic transmission section can easily be disturbed. Furthermore, tighter requirements regarding data security and protection of personal data can be met because the downlink can only be created when the external acoustic receiver is brought into direct contact with the skin. Remote read-out of data is not possible.

In another exemplary embodiment of the invention the implantable transponder may form an independent unit or may be integrated in an implant. According to a further design of the invention it may be integrated in an implantable telemetry unit or coupled to such a unit. The data can be transmitted from an external transmitting unit to the implanted transponder by electromagnetic vibrations and/or waves, according to another design of the invention. However, the uplink may also be designed as an acoustic section.

A transponder can be provided either exclusively for the reproduction of permanently stored data (read-only transponder), e.g. to request an article or serial number of an implant, or may also contain a modifiable memory, which is fully or partially writable by means of an external unit, e.g. for storing and reproducing patient data.

Transformation elements for transforming acoustic waves into electric signals or for transforming electric signals into acoustic waves may be piezo elements or magnetostrictive elements such as microphone or loudspeaker technologies.

The above mentioned features with respect to exemplary embodiments of the system may also be used for a method for transmitting data to an implant.

BRIEF DESCRIPTION OF THE DRAWINGS

In the following, exemplary embodiments of the present invention will be specified for further explanation and for better understanding with reference to the attached drawings.

DETAILED DESCRIPTION OF THE PREFERRED EMBODIMENTS

Similar or relating components in the several figures are provided with the same reference numerals. The view in the figures is schematic and not fully scaled.

Figure 1:
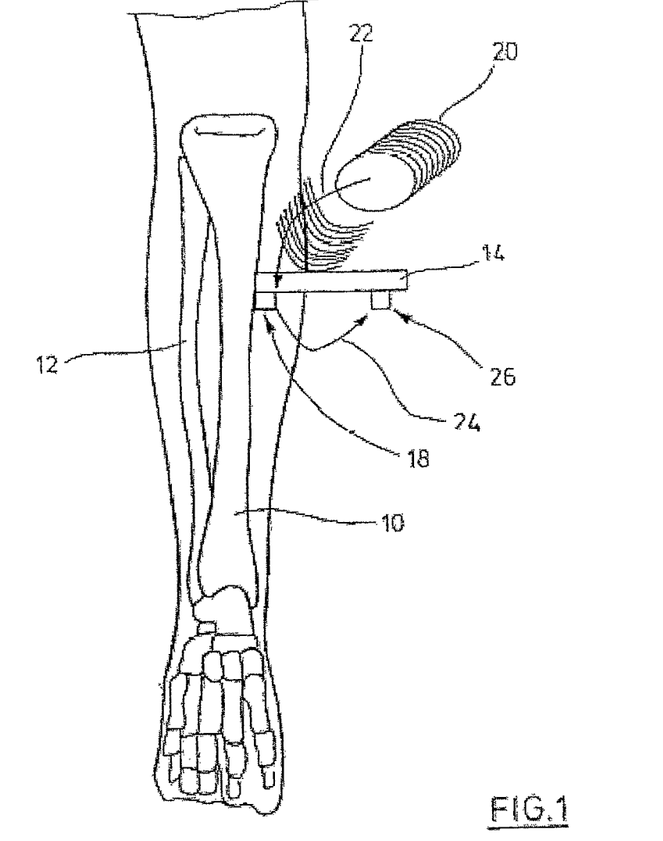
FIG. 1 shows a diagrammatic representation with a telemetry system according to the invention.

FIG. 1 shows diagrammatically a human leg, with shin bone 10 and fibula 12. A fracture of the shin bone 10 is represented, which is treated externally with a fixator. This is not shown in detail. Instead, only a pin is shown at 14, such as the pin normally used in such devices. As is well known, at least one such pin is screwed into each fracture segment, which pins are clamped against one another outside the bone by suitable rods, in order to position the bone fragments one against the other. Since such treatment is well known it will not be described in detail here.

A transponder unit 18 is fitted on pin 14 close to shin bone 10. It contains an electromagnetic first receiving unit 31 and an acoustic transmitting unit 32. Both are encapsulated hi a metal housing. The acoustic transmitting unit 32 is fitted to pin 4 by means of a suitable converter. The energy for first receiving unit 18 is coupled electrically by an electromagnetic transmitter 20. An electromagnetic uplink 21, 22 is therefore provided.

A measuring unit, not shown, which is either contained in the housing of unit 18 or can be connected to it, is coupled to the first receiving and internal transmitting unit 18. This unit records required data of a physical and/or chemical nature, for example data which provide information on the healing process of the fracture, on the dynamic loading of the bone etc. The measured data are suitably processed so that they can be coupled by means of the acoustic internal transmitting unit 32 and the acoustic converter to pin 14. The pin therefore constitutes the acoustic transmission section (downlink 24). An acoustic receiver 26, which receives the data coming from the acoustic transmitter, sits at the distal end of pin 14. They can then be suitably processed by a data processor 40 or the like.

In the embodiment shown FIG. 1 the acoustic converter 33 of the external downlink receiver 26 is installed on a component outside the body, a transcutaneous pin 14. The acoustic telemetry transmission takes place exclusively through the material of the implant system. Alternatively it is possible to fit the acoustic converter of the external downlink receiver on the body surface (skin). The acoustic telemetry transmission then takes place through the implant material, bone an soft part tissue and the skin.

Figure 2:
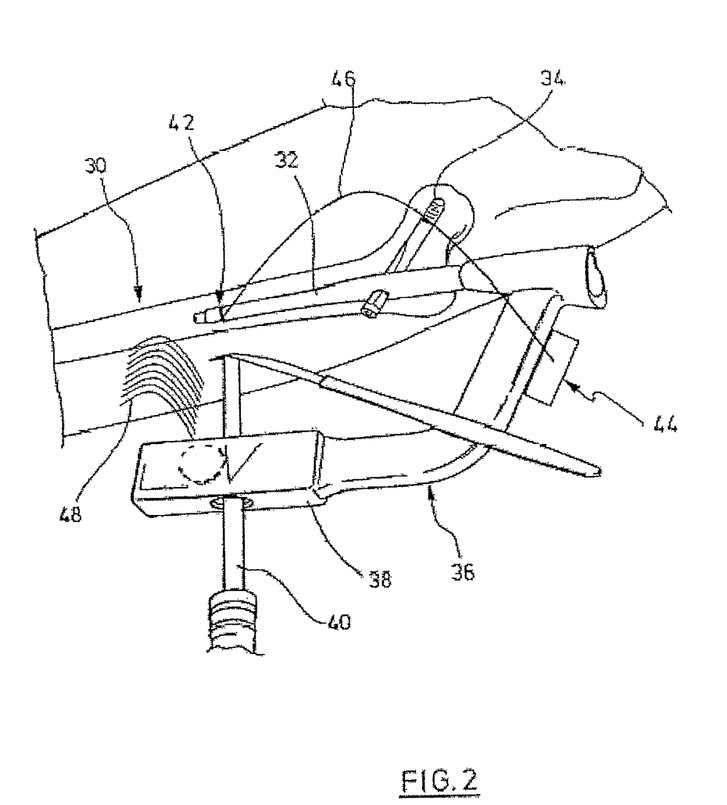
FIG. 2 shows another diagrammatic representation of an application of a telemetry system according to the invention.

FIG. 2 shows the process of implanting a so-called gamma nail into the proximal femur 30. The nail consists of an interlocking nail 32 and a femur neck pin 34 insert obliquely in it. Interlocking nail 32 is driven in by means of a target device 36, which is permanently fitted to the proximal nail end. It therefore also serves as a striking element. Holes are provided on the target arm 38 of target instrument 36 for locating transverse holes in nail 32. A corresponding drilling sleeve is shown at 40. The implanting system described is generally known and will not be described in further detail here.

A receiving and transmitting unit 42 is installed in the distal end region of nail 32, comparable to receiving and transmitting unit 18 in FIG. 1. It contains one measuring unit and is connected to a measuring unit on or in the nail for measuring data of interest to the operating physician. An acoustic receiving unit is installed at 44 on target instrument 36. During the operation the acoustic transmitter in unit 42 communicates with the acoustic receiver 44 via nail 32 and the target strap of instrument 36. These parts are therefore used as acoustic wave guides. This is denoted by 46 (downlink). The power is supplied by an electromagnetic uplink 48. The control data for unit 32 and the measuring unit may also be transmitted electromagnetically.

Figure 3:
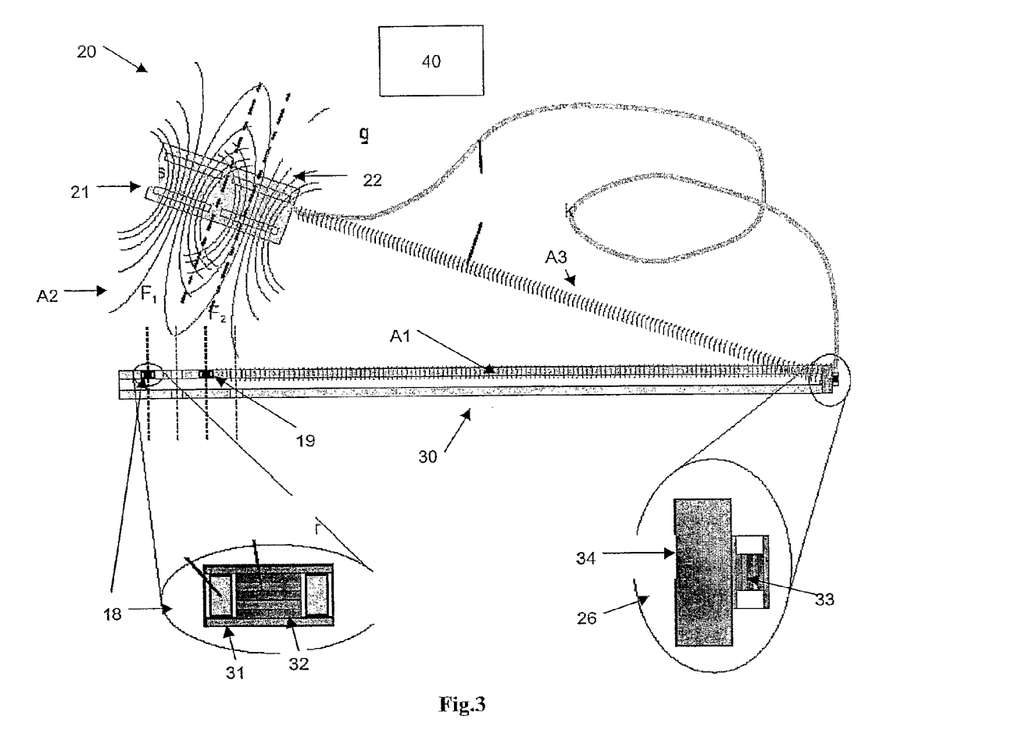
FIG. 3 shows a targeting device by using an active nail tip and an distal targeting device according to one exemplary embodiment of the invention.

FIG. 3 shows an exemplary embodiment, wherein principles of embodiments the invention is used in a electromagnetic and acoustic targeting system. The implant 30 comprises a nail that is adapted to be driven into for example a bone. The nail 30 is fixed by pins that were implement in bores of the nail 30. During operation it is the task of the targeting system to show the user where the bores of the nail 30 are located. Therefore the nail 30, also called Active Nail Tip (ANT), comprises transponders 18, 19 integrated into the nail 30 and located between the bores of the nail 30. The transponders 18,19 are activated by an electromagnetic signal and emits a response signal which is used for tracking. According to embodiments of the present invention, the transponders 18, 19 are hybrid transponders, comprising a first receiving unit 31 and a transmitting unit 32, whereby the first receiving unit 31 may comprise a receiving coil 31 that is activated by electromagnetic energy external transmitting unit 20. Thereby, the receiving coil 31 activates the transmitting unit 32, that emits accordingly acoustical waves and send these acoustical waves via a first transmission section A1 to a second receiving unit 26 placed on the opposite end of the nail 30. The second receiving unit 26 may in turn comprises an acoustic transducer element 33 and a further transmitting element 34 for transforming the acoustic waves in for example electrical signals and for sending them to a processor 40 or a external transmitting device 20 or targeting device 20.

For an optimized targeting system, the distal targeting device (DTD) 20 may comprise a plurality of transmitting coils 21, 22. The working principle for detecting the bores of a nail 30 with an active nail tip will be described in the following: A coil array in the DTD 20 emits different electromagnetic frequencies by each of the coils, 41,0 kHz, 41.1 kHz to 41.9 kHz for 10 coils, for instance. The receiving coils 31 in the transponders 18 are picking up those frequencies and feed them into the internal transmitting units 32. These acoustic transducers 32 in the hybrid transponders 18 are transmitting respective acoustic ultrasound waves. The internal transmitting units 32 respectively transmits depending on the frequencies and depending on the signal strength of the electromagnetic waves acoustic ultrasound waves. These ultra sound waves are now transmitted via the first transmission section A1 to the second receiving element, which may be also an acoustical transducer 26. The second receiving element 26 is located at the proximal end of the nail 30 and is picking up the acoustic ultrasound waves and converts them into an electric signal, which depends on the frequencies and the signal strength. The electrical signal may be linked wireless or by cable to the DTD 20 or to the processor 40 and is evaluated by the digital signal processor 40 regarding the intensities of the signals of each frequency. If the signal strength of each frequency is equal, then the distance between a first transmitting coil 21 of the targeting device and the transponder 18 is equal to the distance between a second transmitting coil 22 of the transmission unit 20 and the further transponder. If the bore is located between the transponders 18 and 19, the targeting device is positioned correctly.

The signals from more than one transponder 18, 19 would be distinguished by assigning different frequency bands to them. There may be used a couple of frequencies, for example around 41 kHz for one transponder 18 and another set of frequencies, for example around 65 kHz for the other transponder 19. Any other pair of frequencies may also be applied.

Instead of using the nail as an acoustic waveguide also the patient s tissue might be used. In this case the acoustic receiver would be attached to the patient's skin in the vicinity of the nail s distal end.

Instead of using a frequency multiplex system, which is exemplary chosen in the embodiment of FIG. 3, in order to distinguish different transmission coil signals 31, a time multiplex system may be used as well. In this case, the different transmitting coils 21, 22 would be activated successively, only one transmitting coil 21,22 being active at a time. This approach would further reduce system complexity as only one signal generator is required which can be timemultiplexed to the coil array by a power switch.

Alternatively a code multiplex system may be used to apply different digital codes to the different coils of the transmission coil array. Signals originating from different transmission coils can be identified according to their coding.

The present invention may also used in connection with a so called RFID system. Therein, the implant respectively the first internal receiving unit 31 is passively installed to the implant 30. In case that the implant 30 is passing an external transmitting unit, the internal first receiving unit 31 is activated by the transmitting coils 21, 22 of the external transmitting unit 20 and datas are sent automatically. Thus, several information, such as serial numbers, material compositions or patient data, may be sent to a host automatically.

At this point it has to be mentioned that the described data transmission system may also be realized by means of further embodiments. Thereby, it is clear for a person skilled in the art that the features described with these further embodiments may also be combined with features of the embodiments described above:

In one exemplary embodiment a data transmission system connected to an implant may be characterised by a measuring unit that can be implanted with the implant for measuring at least one physical or chemical value on the implant or in the region thereof, an internal transmitting unit that is integrated with the measuring unit or can be coupled to and implanted with it, an extracorporeally arranged receiving unit, a first transmission section (downlink) between the internal transmitting and extracorporeal receiving unit, an extracorporeally arranged external transmitting unit, an implantable receiving unit that can be actuated by the external transmitting unit, a second transmission section (uplink) between the external transmitting and internal receiving unit, via which the measuring unit and internal transmitting unit are actuated, wherein the first transmission section operates with acoustic vibrations or waves.

In an exemplary embodiment the second transmission section operates with electromagnetic waves.

In an exemplary embodiment both data and energy for operation of the measuring unit and the internal receiving and transmitting unit are transferred via the second transmission section.

In an exemplary embodiment a third transmission section is in operation for transmitting data and acoustic vibrations or waves.

In an exemplary embodiment the measuring unit and the internal receiving and transmitting unit are encapsulated in a body-compatible material.

In an exemplary embodiment the internal transmitting unit is acoustically coupled to the implant.

In an exemplary embodiment the external transmitting unit and/or the acoustic external receiving unit are designed for coupling to the skin.

In an exemplary embodiment in the case of an internal implant with transcutaneous transit, by means of a metal pin or the like, the latter forms the first transmission section.

In an exemplary embodiment the measuring unit and the internal transmitting and receiving unit are installed on an intramedullar nail, and the external acoustic receiving unit can be detachably installed on the associated end of the nail or on a driving-in instrument connected to the nail.

In an exemplary embodiment a data transmission system connected to an implant is provided, comprising an implantable transponder with an internal transmitting unit, an extracorporeally arranged receiving unit, a first transmission section (downlink) between the internal transmitting and extracorporeal receiving unit, an electromagnetic energy supply by means of inductive and/or capacitive coupling along an uplink section, wherein the first transmission section operates with acoustic vibrations or waves.

In an exemplary embodiment the implantable transponder forms an independent unit or is integrated in the implant.

In an exemplary embodiment the implantable transponder is integrated in an implantable telemetry unit or is coupled to such a unit.

In an exemplary embodiment a data transmission takes place from the external transmitting unit to the implanted transponder by means of electromagnetic vibrations and/or waves.

In an exemplary embodiment the data transmission takes place from the external transmitting unit to the implanted transponder by means of acoustic vibrations and/or waves.

In an exemplary embodiment the implanted acoustic transmitting unit is coupled acoustically to the bone, implant or soft part tissue.

In an exemplary embodiment the external acoustic transmitting and/or receiving unit is coupled to the skin or an external part of a transcutaneous implant.

In an exemplary embodiment the implanted transponder contains a memory with permanently stored data (read-only transponder).

In an exemplary embodiment the implanted transponder contains a modifiable writable memory.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A data transmission system connected to a bone implant, the data transmission system comprising:
   an extracorporeally arranged external transmitting unit;
   an implantable internal first receiving unit adapted to be actuated by the external transmitting unit;
   an internal transmitting unit adapted to be coupled to and integrated into the bone implant;
   a first transmission section between the external transmitting unit and the internal first receiving unit, via which the internal transmitting unit is actuated;
   a second transmission section through the bone implant between the internal transmitting unit and a second receiving unit; and
   wherein the second transmission section operates with acoustic vibrations or acoustic waves and; wherein the bone implant is an intramedullary nail.

2. The data transmission system according to claim 1, wherein the first transmission section operates with electromagnetic waves.

3. The data transmission system according to claim 2, wherein the first transmission section is adapted for transmitting both data and energy for operating at least one of the internal receiving unit or the internal transmitting unit.

4. The data transmission system according to claim 1, wherein the external transmitting unit comprises at least one transmitting coil for transmitting data and energy via the first transmission section.

5. The data transmission system according to claim 1, wherein the first receiving unit comprises a receiving coil.

6. The data transmission system according to claim 1, wherein the internal transmitting unit includes a first acoustic transducer element.

7. The data transmission system according to claim 1, wherein the second receiving unit comprises an acoustic transducer element and a transmitting element,
wherein the second receiving unit acoustic transducer element is adapted for transforming acoustic waves into electrical signals;
wherein the receiving unit transmitting element is adapted for transmitting the electric signal to the external transmitting unit via a third transmitting section.

8. The data transmission system according to claim 7, wherein the third transmission section is adapted for transmitting data by acoustic vibrations or waves, electric signals or electromagnetic waves, wherein the third transmitting section consists of a cable connection or a wireless connection.

9. The data transmission system according to claim 1, further comprising a processor unit,
whereby the processor unit is adapted for being fixed to at least one of the second receiving unit or to the external transmitting unit; and
whereby the processor unit is adapted for evaluating the data received by the second receiving unit.

10. The data transmission system according to claim 1 wherein the internal transmitting unit is acoustically coupled to the implant.

11. The data transmission system according to claim 1, wherein the external transmitting unit and/or the second receiving unit are designed to be coupled acoustically to at least one of the skin or an external part of a transcutaneous implant.

12. The data transmission system according to claim 1, wherein the implant is an internal implant with transcutaneous transit, wherein the second transmission section is formed by means of a metal pin.

13. The data transmission system according to claim 1, wherein the internal transmitting unit and the first receiving unit are installed on the intramedullary nail, and the second receiving unit can be detachably installed on the associated end of the nail or on an insertion instrument connected to the nail.

14. The data transmission system according to claim 1, further comprising a measuring unit adapted to be implanted with the implant for measuring at least one physical or chemical value on the implant or in the region thereof.

15. The data transmission system according to claim 14, wherein at least one of the internal transmitting unit or the first internal receiving unit are integrated with the measuring unit or a transponder.

16. The data transmission system according to claim 1, further comprising a first transponder unit;
wherein the first transponder unit comprises the first internal receiving unit and the internal transmitting unit; and
wherein the transponder unit is encapsulated in a body-compatible material.

17. The data transmission system according to claim 16, wherein the implantable first transponder unit forms an independent unit or is integrated in the implant.

18. The data transmission system according to claim 16, wherein the implantable first transponder unit is integrated in an implantable telemetry unit or is coupled to such a unit.

19. The data transmission system according to claim 16, wherein a data transmission takes place from the external transmitting unit to the implantable first transponder unit by means of electromagnetic vibrations or waves.

20. The data transmission system according to claims 1, wherein the internal transmitting unit is capable of being coupled acoustically to the bone, the implant or a soft tissue.

21. The data transmission system according to claim 18, wherein one of the measuring unit and the implanted first transponder unit contains a memory with permanently stored data.

22. The data transmission system according to claim 16, further comprising a second transponder unit;
wherein the first transponder unit and the second transponder unit are located on the implant;
wherein the second transponder unit comprises an internal third receiving unit and a second internal transmitting unit;
wherein the external transmitting unit comprises at least two transmitting coils for transmitting data and energy via the first transmission section to the third internal receiving unit of the second transponder unit;
wherein the receiving coils of the first transponder unit and the second transponder unit are adapted for activating the internal transmitting units according to the transmitted data originating from the external transmitting unit;
wherein the internal transmitting units of the first transponder unit and the second transponder unit transmit the data to the second receiving unit via the second transmission section; and
wherein the second receiving unit or the transmitting unit are adapted for analyzing the position of the transmitting unit relative to the first transponder unit and the second transponder unit.

23. A data transmission system connected to a bone implant, the data transmission system comprising:
an extracorporeally arranged external transmitting unit;
an implantable internal first receiving unit integrated into the bone implant adapted to be actuated by the external transmitting unit;
an internal transmitting unit adapted to be coupled to and integrated into the bone implant;
a first transmission section between the external transmitting unit and the internal first receiving unit, via which the internal transmitting unit is actuated;
a second transmission section through the bone implant between the internal transmitting unit and a second receiving unit; and
wherein the second transmission section operates with acoustic vibrations or acoustic waves and; wherein the bone implant is an intramedullary nail.

24. The data transmission system of claim 23 wherein the internal first receiving unit is located at a first location on the bone implant and the second receiving unit is located at a second location along the bone implant spaced from the first location.

25. The data transmission system of claim 24 wherein the first location is adjacent a bore in the bone implant and the second location is adjacent an end of the bone implant.

26. A data transmission system connected to a bone implant, the data transmission system comprising:
an extracorporeally arranged external transmitting unit;
an implantable internal first receiving unit adapted to be actuated by the external transmitting unit;
an internal transmitting unit adapted to be acoustically coupled to and integrated into a metal body portion of the bone implant the internal transmitting unit producing and transmitting acoustic data to the implant metal body;

a first transmission section between the external transmitting unit and the internal first receiving unit, via which the internal transmitting unit is actuated;

a second transmission section through the metal body porting of the bone implant between the internal transmitting unit wherein the second transmission section operates exclusively with acoustic vibrations or acoustic waves transmitted through the implant metal body portion; and; wherein the bone implant is an intramedullary nail; and a second receiving unit acoustically coupled to the implant metal body portion at a location along the second transmission section spaced from the first receiving unit having an acoustic transducer for receiving the acoustic data transmitted through the implant second transmission section and converting it into electrical signals.

27. The data transmission system according to claim 26, wherein the second receiving unit comprises the acoustic transducer element and further comprises a transmitting element for transmitting the electrical signals, and wherein the receiving unit transmitting element is adapted for transmitting the electric signal to the external transmitting unit via a third transmitting section.

\* \* \* \* \*